(12) United States Patent
Greter (10) Patent No.: US 9,370,630 B2
(45) Date of Patent: Jun. 21, 2016

(54) MEDICAL SPRAY-HEAD WITH COMPRESSED GAS ASSISTANCE

(75) Inventor: Andy Greter, Baar (CH)

(73) Assignee: MEDMIX SYSTEMS AG, Rotkreuz (CH)

( * ) Notice: Subject to any disclaimer, the term of this patent is extended or adjusted under 35 U.S.C. 154(b) by 415 days.

(21) Appl. No.: 13/878,632

(22) PCT Filed: Sep. 15, 2011

(86) PCT No.: PCT/CH2011/000217
§ 371 (c)(1),
(2), (4) Date: Apr. 10, 2013

(87) PCT Pub. No.: WO2012/048434
PCT Pub. Date: Apr. 19, 2012

(65) Prior Publication Data
US 2013/0206137 A1    Aug. 15, 2013

(30) Foreign Application Priority Data
Oct. 15, 2010   (CH) ...................................... 1698/10

(51) Int. Cl.
*A61M 11/02* (2006.01)
*A61B 17/00* (2006.01)
*B05C 17/005* (2006.01)
*B05B 7/06* (2006.01)
(Continued)

(52) U.S. Cl.
CPC .......... *A61M 11/02* (2013.01); *A61B 17/00491* (2013.01); *A61M 11/06* (2013.01); *B05B 7/066* (2013.01); *B05B 7/2467* (2013.01); *B05C 17/00593* (2013.01); *A61B 2017/00495* (2013.01); *A61B 2017/00522* (2013.01); *B05C 17/00553* (2013.01)

(58) Field of Classification Search
CPC ............... A61B 17/00491; A61B 2017/00495; A61B 2017/00522; A61M 11/06; A61M 11/02; B05B 7/2467; B05B 7/066
USPC .................................................. 239/399, 311
See application file for complete search history.

(56) References Cited

U.S. PATENT DOCUMENTS

| 4,940,185 | A | | 7/1990 | Fu |
| 5,605,541 | A | | 2/1997 | Holm |
| 5,759,169 | A | * | 6/1998 | Marx ............... A61B 17/00491 128/200.21 |

(Continued)

FOREIGN PATENT DOCUMENTS

| WO | 2007/000066 A1 | 1/2007 |
| WO | 2010/048734 A1 | 5/2010 |

OTHER PUBLICATIONS

International Preliminary Report on Patentability for International Application No. PCT/CH2011/000217 issued Apr. 16, 2013.

*Primary Examiner* — Arthur O Hall
*Assistant Examiner* — Juan C Barrera
(74) *Attorney, Agent, or Firm* — Sughrue Mion, PLLC (57) ABSTRACT

Proposed are a medical spray head (300) for spraying one or more fluid substances with the use of a compressed gas, a spray device equipped therewith, and a method for using the same. In order to avoid too high a gas pressure, the spray head comprises a pressure relief valve (310) which guides the compressed gas out of the spray head if the gas pressure exceeds a threshold pressure. As a result, the risk of gas embolisms occurring during the use of such a spray head for medical purposes is reduced.

29 Claims, 8 Drawing Sheets

(51) Int. Cl.
*B05B 7/24* (2006.01)
*A61M 11/06* (2006.01)

(56) References Cited

U.S. PATENT DOCUMENTS

| | | | |
|---|---|---|---|
| 5,810,885 A | 9/1998 | Zinger | |
| 6,135,358 A | 10/2000 | Ballini | |
| 6,165,201 A * | 12/2000 | Sawhney | A61B 17/00491 604/197 |
| 2003/0209612 A1 | 11/2003 | Hahnen | |
| 2007/0005007 A1 * | 1/2007 | Hoogenakker | A61B 17/00491 604/82 |
| 2009/0108091 A1 * | 4/2009 | Steffen | 239/11 |
| 2009/0127288 A1 * | 5/2009 | Keller | A61B 17/00491 222/108 |
| 2009/0209916 A1 | 8/2009 | Peindl et al. | |
| 2010/0168779 A1 * | 7/2010 | Redl | A61B 17/00491 606/185 |

* cited by examiner

MEDICAL SPRAY-HEAD WITH COMPRESSED GAS ASSISTANCE

CROSS REFERENCE TO RELATED APPLICATIONS

This application is a National Stage of International Application No. PCT/CH2011/000217 filed Sep. 15, 2011, claiming priority based on Swiss Patent Application No. 1698/10, filed Oct. 15, 2010, the contents of all of which are incorporated herein by reference in their entirety.

TECHNICAL FIELD

The present invention relates to a spray head for connection to at least one reservoir with a fluid substance and for spraying this substance with the use of compressed gas, e.g. of compressed air or some other compressed gas such as carbon dioxide.

STATE OF THE ART

Spray heads for spraying one or several substances with compressed gas assistance are used, inter alia, in the medical field, for example for spraying a medical two-component adhesive based on fibrinogen and thrombin. Such so-called fibrin glues are used in medical applications e.g. for closing lesions, for stopping bleeding (haemostasis) or as tissue adhesives for the attachment of skin grafts. For use, such a spray head is connected to one or several reservoirs comprising the substances to be sprayed, e.g. to a single syringe comprising the already pre-mixed adhesive or to a double syringe comprising the components of the adhesive. In order to spray the substances, on the one hand the spray head is provided with compressed gas in order to generate a flow of compressed gas, and on the other hand the user dispenses the substances from the reservoir in order to introduce them into the flow of compressed gas, and thus to atomise them.

Such a spray head is, for example, known from WO 2010/048734. In a central region of the spray head the substances to be sprayed are fed, by way of one or several fluid channels, to nozzle-like fluid outlets at the tip of the spray head. An annular channel for a compressed gas encloses the fluid channels and leads to several gas outlets that are arranged so as to be slightly set back relative to the fluid outlets. During operation a gas flow exits from the gas outlets. This gas flow impacts on the substances exiting the fluid outlets, atomises said substances and transports the resulting spray mist to an intended application region, for example to a wound of a patient, which wound is to be treated.

From the state of the art a multitude of further designs of spray heads are known. Thus, it has, for example, been proposed to centrally supply the compressed gas in the spray head, while the substances to be sprayed are supplied by way of an annular gap or by way of fluid channels arranged decentrally. One example of such a design is stated in U.S. Pat. No. 5,605,541. Furthermore, spray heads are known in which the substances to be sprayed are mixed with the compressed gas in a mixing chamber before the spray mist that was premixed in this manner exits from an outlet nozzle of the spray head. Examples of this are described in US 2003/0209612 or US 2009/0108091. For endoscopic, laparoscopic or other minimally invasive applications, spray heads are known that comprise an elongated tube that can be inserted into the interior of the body by way of a body orifice, and through which tube the substances and the compressed gas are supplied. Examples of this are described in US 2009/0209916 or US 2007/0005007.

In this context it is known to feed the substances to be sprayed and the compressed gas through separate lines to a distal end of the spray head, as is, for example, also described in U.S. Pat. No. 5,810,885.

Irrespective of the concrete design, in compressed-gas-assisted spray heads there is a danger, in the case of excessive gas pressure, of the compressed gas entering blood vessels in the application region, thus causing gas embolism. Even independently of this concrete danger, excessive gas pressure can lead to undesirable results, for example to an uneven spray pattern or to uncontrolled distribution, beyond the intended application region, of the substances to be sprayed. Finally, it can also happen that the substances to be sprayed block the gas outlet channels, and that consequently the gas pressure in the spray head increases suddenly. In unfavourable cases this results in the compressed gas finding its way in an undesirable manner into the fluid channels and from there into the fluid reservoirs in which the substances are held. If the fluid reservoirs are designed as syringes, this can result in the syringe pistons being pushed back. This is highly undesirable.

In order to limit the gas pressure on the spray head it has been known to provide a gas regulator between the source of compressed gas and the spray head, which gas regulator limits to a predetermined maximum value the pressure of the gas that reaches the spray head. However, in this type of gas regulator there is always a danger of malfunction or incorrect operation. Incorrect operation can, in particular, occur in those situations where several different types of spray heads are alternatively connectable to the same gas regulator. In this case the intended operating pressure can differ between spray heads, and there is a danger of operating personnel, during the changeover of a spray head that is operated at higher operating pressure to a spray head that is to be operated at lower operating pressure, forgetting to correspondingly regulate back the gas regulator.

In U.S. Pat. No. 6,135,358 a compressed-gas-assisted device for irrigating the nasal cavities, which device comprises a regulating valve for regulating the gas pressure is proposed. The design of this device means that it is only suitable for the irrigation of nasal cavities, but is not suitable for spraying a medical adhesive or its components. The device is, in particular, not suitable to be connected to one or several reservoirs with the substances to be sprayed.

From U.S. Pat. No. 4,940,185 a spray gun is known that is provided for spraying a substance to be sprayed, for example paint, from a bottle connected to the spray gun. Compressed gas is fed to a spray nozzle. The same compressed gas is also introduced into the bottle in order to build up overpressure in the bottle, and in so doing to transport the substance that is to be sprayed from the bottle to the spray nozzle. In order to prevent excessive pressure building up in the bottle, a safety valve is provided in the feed line of the compressed gas to the bottle, but not in the feed line of the compressed gas to the nozzle. This spray gun is obviously not intended for medical applications, nor does it prevent the compressed gas being able to emanate from the spray nozzle at undesirably high pressure.

PRESENTATION OF THE INVENTION

It is thus an object of the present invention to provide a spray head for spraying at least one fluid substance from an external reservoir by means of a compressed gas, in which spray head the pressure of the compressed gas in the spray head is prevented from rising above a predetermined maximum value.

Thus a spray head for spraying at least one fluid substance with the use of a compressed gas is proposed, which spray head comprises:

at least one fluid connector in order to connect the spray head to at least one fluid reservoir for the substance to be sprayed;

at least one fluid channel that connects the fluid connector to at least one fluid outlet;

a compressed gas connector in order to connect the spray head to a source of compressed gas; and at least one compressed gas channel that connects the compressed gas connector to at least one compressed gas outlet, wherein the fluid outlet and the compressed gas outlet are arranged relative to each other in such a manner that during operation compressed gas exiting the compressed gas outlet impacts on a substance exiting the fluid outlet so as to spray said substance.

The spray head is characterised in that it comprises a pressure relief valve that is configured to discharge/divert compressed gas from the compressed gas channel when the compressed gas has a gas pressure that exceeds a threshold pressure.

Consequently it is possible to ensure directly on the spray head that a predetermined maximum pressure (the threshold pressure) at the compressed gas outlet is not significantly exceeded. In this manner it is possible to effectively prevent the substance from being sprayed at excessive gas pressure. With the use of such a spray head on open body tissue the risk of an embolism occurring is thus significantly reduced. If the spray head is used together with an external gas regulator, the proposed spray head effectively prevents negative consequences of incorrect operation or malfunction of the gas regulator. Because the pressure relief valve is provided on the spray head itself, any malfunctions that might possibly occur between the source of compressed gas or the gas regulator and the spray head do not have any influence on the effective limitation of the gas pressure directly on the spray head.

The pressure relief valve is preferably provided in a region of the compressed gas channel, which region in terms of the direction of flow of the compressed gas is arranged upstream of the compressed gas outlet. Consequently the function of the pressure relief valve is ensured even if the substance to be sprayed were to block the region of the compressed gas outlet.

On the other hand the pressure relief valve is, however, also preferably arranged in a region of the compressed gas channel, which region in terms of the direction of flow of the compressed gas is arranged downstream of the compressed gas connector. In particular it is thus preferable if the pressure relief valve is not provided on a line that is separately connected to the compressed gas connector, but precisely on that part of the compressed gas channel through which part compressed gas actually flows on its way between the compressed gas connector and the compressed gas outlet. In this manner it is ensured that the valve is subjected to the pressure of that gas that flows towards the compressed gas outlet, and it is also ensured that any narrowing or blockage of a separate valve supply line cannot in an undesirable manner influence the pressure on the valve itself.

Depending on the concrete design of the spray head there are various possibilities concerning the location in which the pressure relief valve is provided on the spray head. Thus the pressure relief valve can, for example, be provided in a region of the compressed gas channel, which region at least partly encloses the fluid channel. In some designs of a spray head the spray head can comprise a static mixing element that is arranged in the fluid channel. In order to create a compact spray head, the pressure relief valve can be provided in a region of the compressed gas channel, which region at least partly encloses the region of the fluid channel in which the static mixing element is arranged.

In some designs the spray head can comprise a basic body that defines a longitudinal axis of the device, and can comprise a gas feed pipe that protrudes from the basic body, on which gas feed pipe the compressed gas connector is implemented. The gas feed pipe can, in particular, be tubular in shape. The gas feed pipe then preferably extends at an angle, in particular at an angle of approximately 30°-90°, preferably at an angle of approximately 50°-80°, relative to the longitudinal axis of the device, wherein the inlet end of said gas feed pipe points away from the compressed gas outlet at the basic body. In advantageous embodiments the pressure relief valve is arranged on the basic body and comprises a valve outlet channel that essentially extends parallel to the gas feed pipe, wherein the outlet end of the valve outlet channel also points away from the compressed gas outlet. As an alternative, the pressure relief valve can, however, also be arranged on the gas feed pipe. As a result of this measure the pressure relief valve disturbs as little as possible during application of the spray head, and the compressed gas that escapes through the pressure relief valve is less likely to reach the application region.

Purely as an example the spray head can in principle be designed as set out in the already mentioned application WO 2010/048734, whose content is herein incorporated by reference. The spray head can in particular comprise an inner sleeve, which in said document is referred to as the housing, in which inner sleeve the at least one fluid channel is formed. The spray head can then furthermore comprise an outer sleeve, which in said document is referred to as the cap, which outer sleeve at least partly encloses the inner sleeve. The outer sleeve and the inner sleeve together delimit at least one section of the compressed gas channel. To this effect in a proximal region the outer sleeve can be connected to the inner sleeve so as to provide a seal while its distal open end together with the inner sleeve delimits several gas outlets that are arranged in an annular manner and enclose one or several fluid outlets. A particularly simple and elegant design is obtained if in such a construction both the compressed gas connector and the pressure relief valve are formed on the outer sleeve. In this design the outer sleeve with its cylinder axis defines a longitudinal axis. The pressure relief valve then advantageously comprises a valve outlet channel whose longitudinal direction is arranged relative to the longitudinal axis of the outer sleeve at an angle of between 30° and 90°, preferably of 50° to 80°, the outlet end of the valve outlet channel pointing away from the compressed gas outlet.

However, entirely different designs are also possible, for example elongated designs with an elongated distal tube for endoscopic or minimally invasive applications are possible. In such designs it is preferred if the pressure relief valve is arranged at a distance from the distal end in a proximal terminal region of the tube or proximally of this tube.

The spray head can specifically be designed to spray a medical product (e.g. a medicament or a medical adhesive) or components of such a product. This intended purpose results in various requirements relating to the design, the selection of materials and the dimensioning of the spray head. For example, for this purpose the spray head should be manufactured in particular from medical grade materials, i.e. materials which are pharmacologically and toxicologically safe (suitable plastic and/or suitable metal, for example stainless steel or titanium). For this use the fluid connectors can be designed as Luer connections or as special system connections for compatible system containers. Likewise, the gas inlet can be designed in the form of a Luer connection. Luer connections are standardised conical plug-type connections that optionally can be secured with a Luer lock securing sleeve. Usually a spray head for medical applications should have the smallest possible lateral dimensions (i.e. dimensions across the longitudinal axis of the spray head), which dimensions should not exceed a few centimeters, in particular should not exceed approx. 5 cm, in order to restrict medical personnel as little as possible during application. In contrast to this, in terms of construction as well as for reasons of material selection and dimensioning, in particular commercially available spray guns for spraying paint are obviously not suitable for medical purposes, and furthermore usually have considerably larger lateral dimensions.

In particular, the spray head can be configured to supply two or more components of a multi-component system, e.g. the components of a medicament or of a medical adhesive, separately to the spray head and intermix them only in the spray head or after they have left the spray head. To this effect the spray head can comprise a first fluid connector and a second fluid connector, wherein each of the fluid connectors is designed to connect the spray head to a respective fluid reservoir for a component to be sprayed. The spray head then comprises a first fluid channel that connects the first fluid connector to a first fluid outlet, and a second fluid channel that connects the second fluid connector to a second fluid outlet. The first fluid outlet, the second fluid outlet and the compressed gas outlet are then preferably arranged relative to each other in such a manner that during operation compressed gas exiting the compressed gas outlet mixes with the two components exiting the fluid outlets in order to atomise the components and to spray them together. In particular, in terms of the direction of flow of the compressed gas, to this effect the fluid outlets can be arranged downstream of the compressed gas outlet or of the compressed gas outlets.

While the invention is not limited to a particular type of pressure relief valve, particular designs are preferred due to their simplicity, robustness and economical production. Thus the pressure relief valve can, in particular, comprise an elastic closure body that is attached to a valve base in such a manner that because of its intrinsic elasticity it closes a valve outlet channel or a valve opening, provided the gas pressure does not exceed the threshold pressure. The closure body can, for example, be an elastic disc that is attached centrally to the valve base. As an alternative, the valve can also be designed as a mushroom-type valve, frequently referred to as an umbrella valve. In this case the closure body is designed so as to be umbrella-like. In such designs, when the threshold pressure is exceeded, the pressure-related force lifts the closure body against the elastic restoring force of the closure body itself from the valve outlet channel.

As an alternative, the pressure relief valve can comprise a rigid, movable closure body that is spring-loaded in such a manner that it closes a valve outlet channel provided the gas pressure does not exceed the threshold pressure. In this case the closure body can, for example, be a closure ball or a closure disc.

Furthermore, it is possible, for example, for the pressure relief valve to comprise an elastic sleeve that encloses a tubular section of the spray head on the outside, and due to its elasticity closes at least one valve outlet channel provided in the tubular section, as long as the gas pressure does not exceed the threshold pressure.

The present invention furthermore also relates to a complete spray device for spraying a medical product (e.g. a medicament or a medical adhesive). Said spray device comprises:

- at least one fluid reservoir with a fluid medical substance contained therein;
- a spray head of the type described above, which spray head is connectable to the fluid reservoir; and
- a dispensing device for dispensing the substance through the spray head.

The fluid reservoir can, for example, be designed in the manner of a cylindrical syringe body with an outlet and a piston that is movable in the syringe body, and the dispensing device can then comprise a piston rod in order to advance the piston in the syringe body in the distal direction and in this manner dispense the substance from the fluid reservoir.

The spray device can also be designed for spraying at least two components of a medical product (e.g. the components of a medicament or of a medical adhesive). In this case the spray device comprises:

- at least two fluid reservoirs, each comprising a component, received therein, of the medical product;
- a spray head of the type provided above, which spray head can be connected to the reservoirs, wherein the spray head comprises at least two fluid connectors for connecting the spray head in each case to an outlet of the fluid reservoirs, and at least two fluid channels that connect the fluid connectors to fluid outlets of the spray head; and
- a dispensing device for dispensing the components through the spray head.

In this embodiment the fluid reservoirs can, for example, be arranged in the manner of a double syringe, multiple syringe, double cartridge or multiple cartridge with two or more cylindrical containers arranged parallel to each other, each comprising an outlet and a displaceable piston, wherein each of these containers delimits a fluid reservoir. The dispensing device can then comprise two or more piston rods that can optionally be interconnected in order to advance the pistons in the distal direction and in this way dispense the components from the fluid reservoirs.

Finally, the present invention also relates to the use of a spray head or of a spray device of the type provided above for spraying a medical product (in particular a medicament or a medical adhesive) or components of such a medical product, in particular a fibrin glue or the components of a fibrin glue. In such a method for spraying a medical product or its components, in particular the following steps are carried out:

- providing the medical product or its components in each case in a reservoir;
- connecting the fluid connector or the fluid connectors of the spray head to the outlet of the reservoir or to the outlets of the reservoirs;
- supplying compressed gas to the compressed gas connector of the spray head so that the compressed gas flows out through the compressed gas outlet or the compressed gas outlets;
- dispensing the medical product or the components through the fluid outlet or the fluid outlets in order to spray the product or the components by means of the compressed gas; and
- discharging compressed gas through the pressure relief valve if the pressure relief valve opens.

In such a method it can be provided for terminating the spraying process if compressed gas exits the pressure relief valve, because this indicates incorrect operation or a malfunction. In particular if the product is a medical adhesive, in this manner the risk of a gas embolism can be further reduced.

BRIEF DESCRIPTION OF THE DRAWINGS

Below, preferred exemplary embodiments of the invention are described with reference to the drawings that are only used for explanation and are not to be interpreted as being limiting. The following are shown in the drawings.

DESCRIPTION OF PREFERRED EMBODIMENTS

In this document designations of directions are used as follows: the term "distal direction" refers to the direction into which discharge of the substances to be sprayed takes place. The term "proximal direction" refers to the direction that is opposite to the aforesaid.

Figure 1:
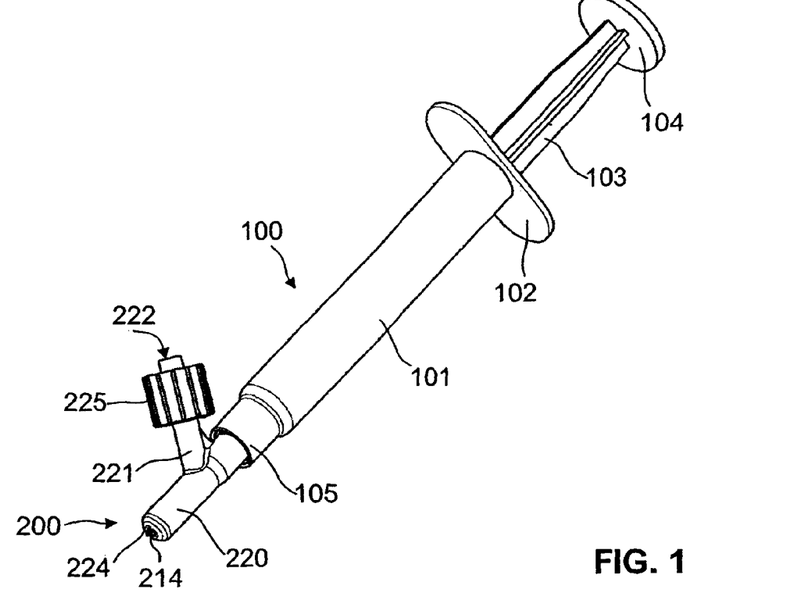
FIG. 1 a perspective view of a syringe with a spray head affixed thereto.
Figure 2:
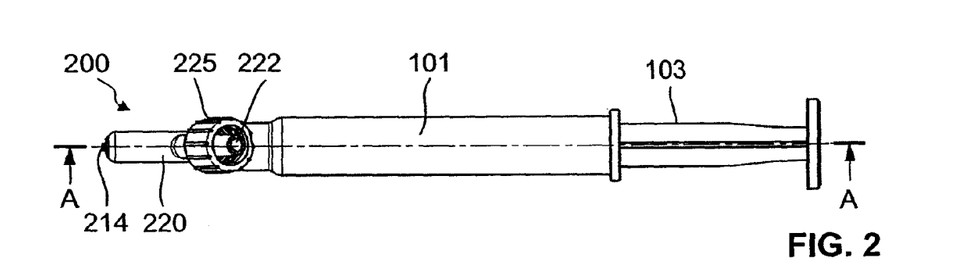
FIG. 2 a top view of the syringe and of the spray head of FIG. 1.
Figure 3:
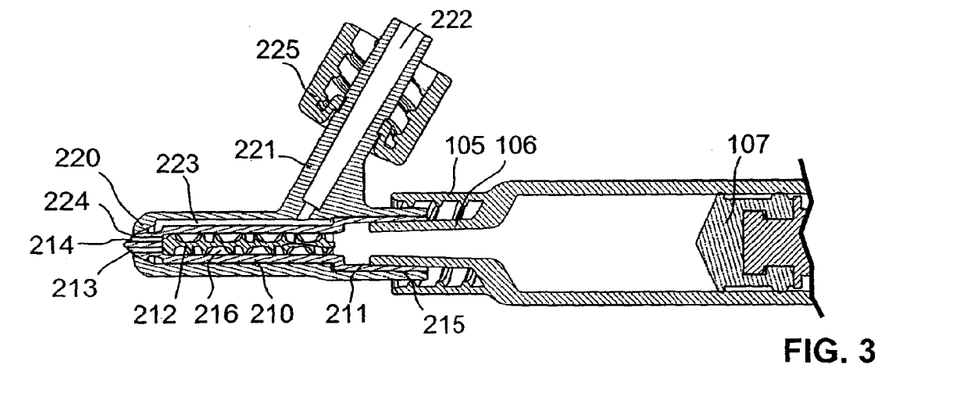
FIG. 3 an enlarged part of a longitudinal section of the syringe and of the spray head in the plane A-A of FIG. 2.

FIGS. 1 to 3 show a syringe 100 with a spray head 200 affixed thereto, which spray head 200 is not designed according to the invention and which is shown to illustrate a possible basic design of a spray head. The syringe 100 comprises a cylindrical syringe body 101 whose proximal end is provided with two opposing radially projecting holding flanges 102. In the interior of the syringe body a slidable piston 107 together with the syringe body delimits a fluid reservoir. The piston 107 can be advanced in the syringe body in the distal direction by means of a piston rod 103 with a thumb rest 104 in order to eject a fluid product through an outlet region 106 from the fluid reservoir.

The spray head 200 comprises an inner sleeve 210 that is enclosed by an outer sleeve 220. The inner sleeve 210 and the outer sleeve 220 together form a basic body of the spray head. The inner sleeve 210 delimits a central fluid channel 216 that extends from a widened proximal fluid connector 211 to one or several nozzle-like distal fluid outlets 214. In the fluid channel a static mixing element 212 with a multitude of helical mixing blades arranged one behind the other has been inserted. Between the fluid connector 211 and the fluid outlets 214 the inner sleeve on the outside comprises a cylindrical main section that in the distal direction on the outside is followed by a short annular recess. This recess in turn is followed by a tip 213. The tip 213 comprises several (in the embodiment shown four) longitudinally-extending webs that merge in a point towards the distal end, between which webs several gas outlet channels are formed that taper towards the distal end and that are inclined towards the central longitudinal axis.

The outer sleeve 220 has been slid from the distal end onto the inner sleeve 210. In this arrangement a torus 215 at the inlet region of the inner sleeve 210 engages a complementary annular groove in the delimitation wall of the outer sleeve 220 in such a manner that towards the proximal end of the spray head a gas-proof connection between the inner sleeve and the outer sleeve is ensured. In the region of the main section of the inner sleeve the outer sleeve 220 extends at least in part at a radial distance from the inner sleeve 210 and together with the inner sleeve forms one or several longitudinally extending gas distribution channels 223. In the region of the distal end of the spray head the gas distribution channels 223 end at the annular recess of the inner sleeve that together with the outer sleeve in this region delimits an annular space.

At its distal end the outer sleeve comprises a central opening which conically tapers off in the distal direction. The wall region of the outer sleeve, which wall region delimits this opening, rests against the webs of the tip 213, thus delimiting towards the radial outside the gas outlet channels formed between the webs. The gas outlet channels connect the annular space to several gas outlets 224 that are arranged so as to be set back slightly from the fluid outlets 214 and enclose them in a ring-shaped manner.

The outer sleeve 220 comprises a gas feed pipe 221 that radially protrudes obliquely to the longitudinal direction, which gas feed pipe 221 forms a compressed gas connector. The gas feed pipe 221 delimits a gas supply channel 222 that exits into the gas distribution channels 223. The gas supply channel 222 and the gas distribution channels 223 in this manner jointly form a compressed gas channel that extends from the compressed gas connector to the gas outlets.

For spraying a fluid product contained in the syringe 100, the spray head 200 is first connected to the outlet region 106 of the syringe 100, as shown in FIGS. 1 to 3. For this purpose the outlet region 106 of the syringe 100 is designed as a male Luer connector with a rigid securing sleeve 105. The inlet region 211 of the spray head 200 is correspondingly designed as a female Luer connector with a short external thread. In this manner a reliable connection between the syringe and the spray head is ensured.

At this point a compressed gas hose is placed onto the gas feed pipe 221. To this effect the free end of the gas feed pipe is designed as a male Luer connector with a rotatably affixed securing sleeve 225. Compressed gas is then fed through the gas supply channel 222 and by way of the gas distribution channels 223 and the annular space reaches the gas outlets 224 where it exits in the form of several fine gas jets. As a result of pressure exerted onto the piston rod 103, the product to be sprayed is then dispensed through the central fluid channel and the fluid outlet or outlets 214, and as a result of the gas jets it is atomized and sprayed. In this arrangement the static mixing element 212 is used to mix and homogenise the product prior to it leaving the spray head.

This fundamental design of the spray head 200 is similar to the design of the spray head according to WO 2010/048734 and, as far as further details are concerned, reference is made to that document, in particular with respect to possible designs of the tip 213. Said document also shows how a spray head of this fundamental design can be modified in order to feed two components separately to the spray head, and to spray them with or without pre-mixing. Of course, the scope of the present invention also includes such embodiments.

Figure 4:
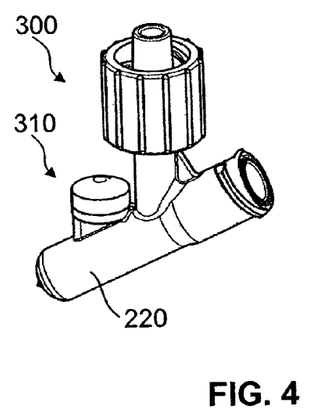
FIG. 4 a perspective view of a spray head according to a first exemplary embodiment of the present invention.
Figure 5:
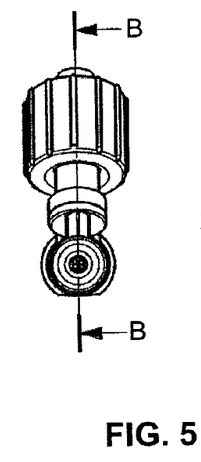
FIG. 5 a front view of the spray head of FIG. 4.
Figure 6:
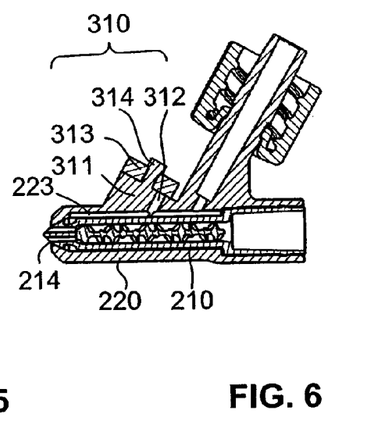
FIG. 6 a central longitudinal section of the spray head in the plane B-B of FIG. 5.
Figure 7:
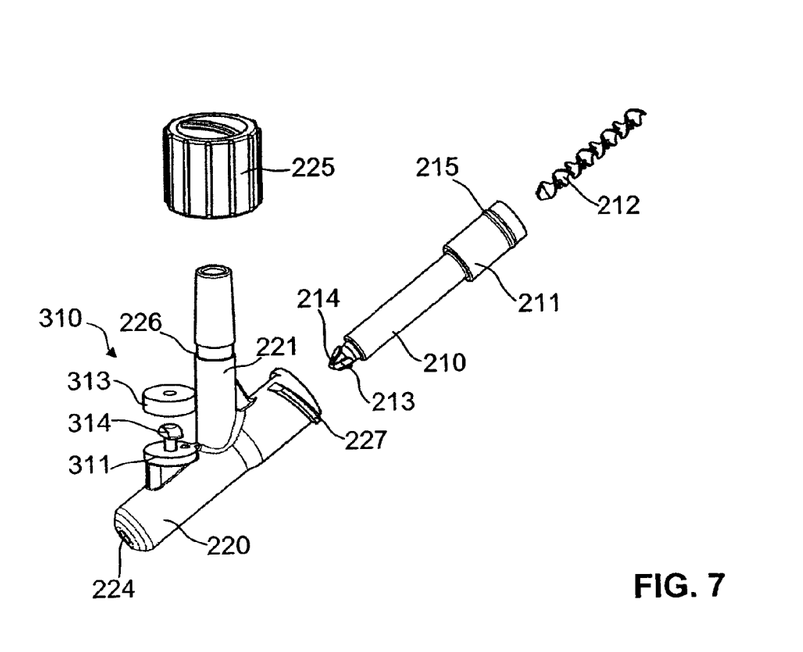
FIG. 7 a perspective exploded view of the spray head of FIG. 4.

FIGS. 4 to 7 show various views of a spray head 300 according to a first exemplary embodiment of the present invention. In its design and function this spray head corresponds largely to the spray head 200 of FIGS. 1 to 3, and components having the same function are thus designated by the same reference characters as in FIGS. 1 to 3. In addition, in particular FIG. 7 shows that the securing sleeve 225 is rotatably held in an annular groove 226 of the gas feed duct 221; furthermore, in particular, FIG. 4 and FIG. 7 show the external thread 227 by means of which the spray head can be affixed in the securing sleeve 105 of the syringe 100.

In order to limit the pressure of the compressed gas in the spray head, this spray head additionally comprises a pressure relief valve 310. The pressure relief valve comprises a valve base 311 formed on the outer sleeve 220, in which valve base 311 a valve outlet channel 312 is arranged decentrally. This valve outlet channel leads from the gas distribution channels 223, obliquely to the longitudinal direction, radially outwards. A valve disc 313, comprising an elastic material, e.g. silicon, closes the valve outlet channel 312 towards the outside. In this arrangement the valve disc 313 is held to the valve base 311 by means of a holding structure 314 that is spaced apart from the valve outlet channel 312. This holding structure comprises a central stud that projects from the valve base 311, which stud opens up at its free end in a hook-shaped manner.

As long as the gas pressure in the gas distribution channels 223, and thus also in the valve outlet channel 312, does not exceed a defined threshold pressure, the valve disc 313 closes the valve outlet channel 312 so as to provide a seal. However, as soon as the gas pressure exceeds the threshold pressure, the gas pressure exerts such a force on the valve disc 313 that the aforesaid elastically deforms, thus opening the valve outlet channel 312 towards the outside. Consequently, compressed gas exits the valve outlet channel until the pressure is again lower than the threshold pressure, and the valve disc 313 closes the valve outlet channel 312.

In this arrangement the extent of the threshold pressure is determined by several factors. This includes, in particular, the cross-sectional area of the valve outlet channel 312 that is covered by the valve disc 313 as well as the preload/bias, geometry and properties of the material of the valve disc 313. By changing these variables the threshold pressure can be set in a wide range.

Figures 8, 9, 10:
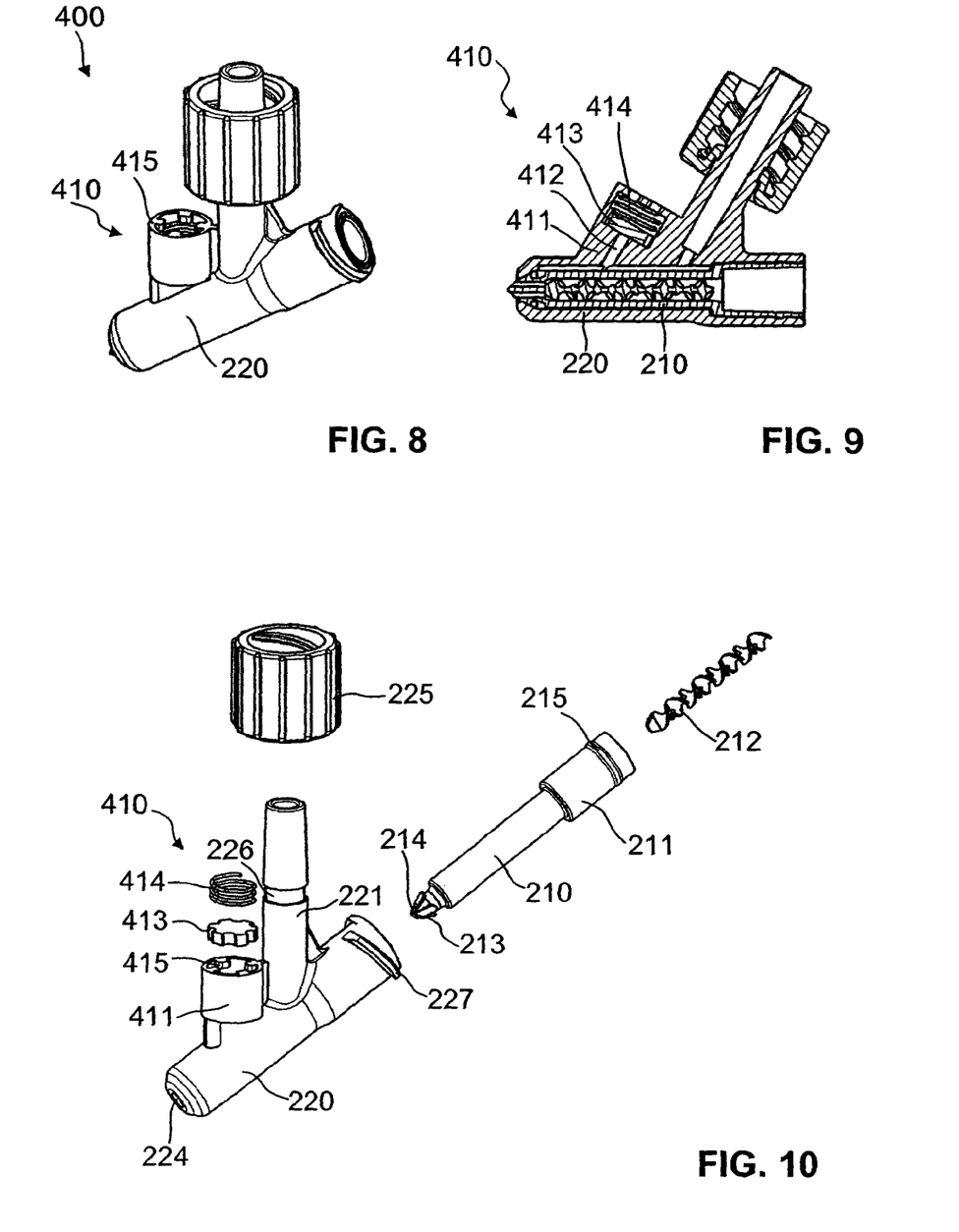
FIG. 8 a perspective view of a spray head according to a second exemplary embodiment of the present invention.
FIG. 9 a central longitudinal section of the spray head of FIG. 8.
FIG. 10 a perspective exploded view of the spray head of FIG. 8.

A spray head 400 according to a second exemplary embodiment of the present invention is shown in FIGS. 8 to 10. Again, the design and function are very similar to that of the spray head 200 of FIGS. 1 to 3, and again the same reference characters are used for components that have the same function.

The spray head 400, too, comprises a pressure relief valve. The pressure relief valve 410 has a valve base 411 with a central valve outlet channel 412. The latter is closed by means of a rigid valve disc 413 which by means of a compression spring 414 is pressed against the free end of the valve outlet channel 412. The compression spring is affixed in the valve base by means of holding lugs 415.

In this exemplary embodiment, too, the valve disc 413 closes the valve outlet channel 412, provided a defined threshold pressure is not exceeded. As soon as the threshold pressure is exceeded, the pressure-related force acting on the valve disc 413 results in the compression spring 414 being compressed so that the valve disc 413 opens the valve outlet channel 412. Again, in this manner during an undesirable increase in pressure, compressed gas can escape until the gas pressure is again below the threshold pressure.

In this exemplary embodiment the threshold pressure can be set by varying the cross-sectional area of the valve outlet channel that is covered by the valve disc 413 and/or the restoring force of the compression spring 414. Furthermore, the elasticity of the valve disc has an influence on the threshold pressure.

Figure 11:
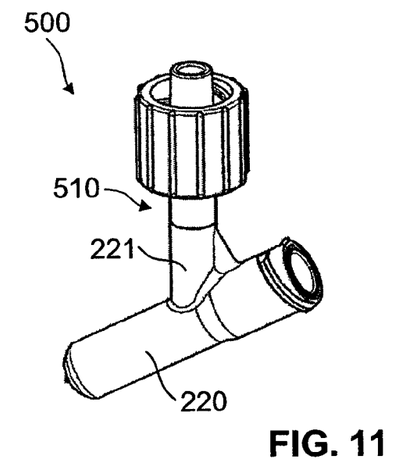
FIG. 11 a perspective view of a spray head according to a third exemplary embodiment of the present invention.
Figure 12:
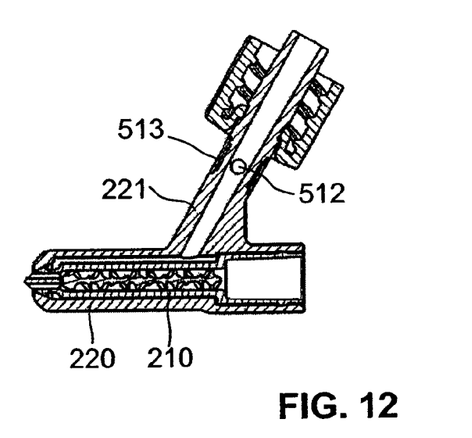
FIG. 12 a central longitudinal section of the spray head of FIG. 11.
Figure 13:
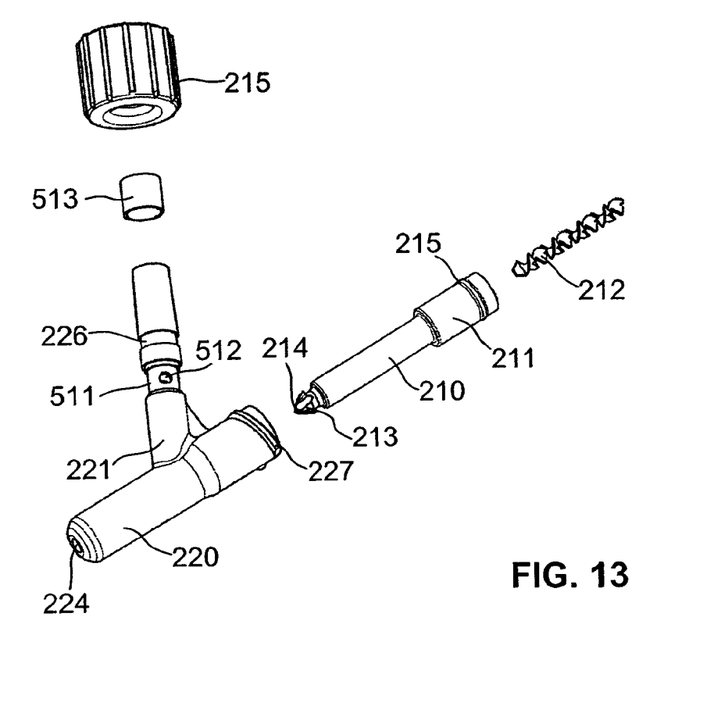
FIG. 13 a perspective exploded view of the spray head of FIG. 11.

A spray head 500 according to a third exemplary embodiment of the present invention is shown in FIGS. 11 to 13. Again, components having the same function are designated by the same reference characters as in FIGS. 1 to 3. The spray head 500 comprises a pressure relief valve in the region of the gas feed pipe 221. To this effect the outside of the gas feed pipe 221 comprises an annular recess 511 (see FIG. 13). In the region of this recess the delimitation wall of the gas feed pipe 221 comprises one or several openings that form one or several valve outlet channels 512. A sleeve-like elastic valve sleeve 513 has been pushed over the recess 511, which valve sleeve 513 can, for example, comprise silicone.

As long as a threshold pressure is not exceeded, the sleeve 513 closes the valve outlet channels 512. As soon as the threshold pressure is exceeded, the compression force of the compressed gas is sufficient to lift the sleeve 513 from the recess 511 so that the valve outlet channels open towards the outside, and compressed gas can escape.

In this exemplary embodiment the threshold pressure can be set in that the opening area covered by the sleeve 513 and/or the properties of the material and the dimensions of the sleeve are changed.

Figure 14:
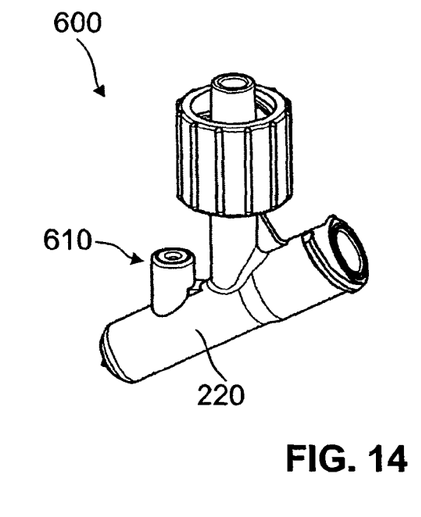
FIG. 14 a perspective view of a spray head according to a fourth exemplary embodiment of the present invention.
Figure 15:
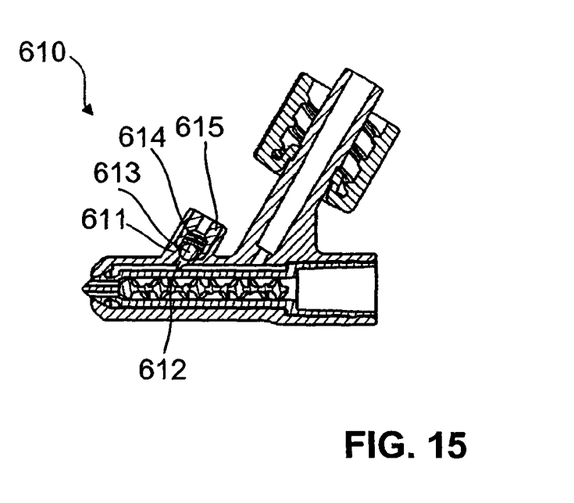
FIG. 15 a central longitudinal section of the spray head of FIG. 14.
Figure 16:
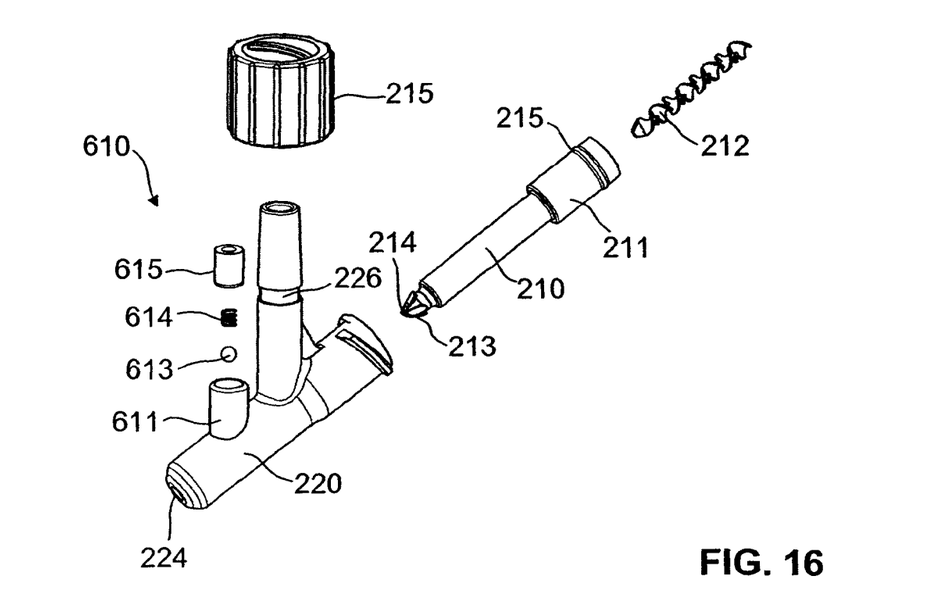
FIG. 16 a perspective exploded view of the spray head of FIG. 14.

FIGS. 14 to 16 show a fourth exemplary embodiment of the present invention. A spray head 600 comprises a pressure relief valve 610 in the form of a ball valve. A valve insert 615 holds a valve ball 613, which has been loaded by a compression spring 614, in a valve base 611 in such a manner that the valve ball 613 closes a valve outlet channel 612. If a threshold pressure is exceeded, the valve ball 613 is lifted from the valve outlet channel 612 and in this manner opens the valve outlet channel 612 towards the outside. In this arrangement the threshold pressure can be set by a suitable selection of the dimensions of the valve outlet channel 612 and the restoring force of the compression spring 614.

Figure 17:
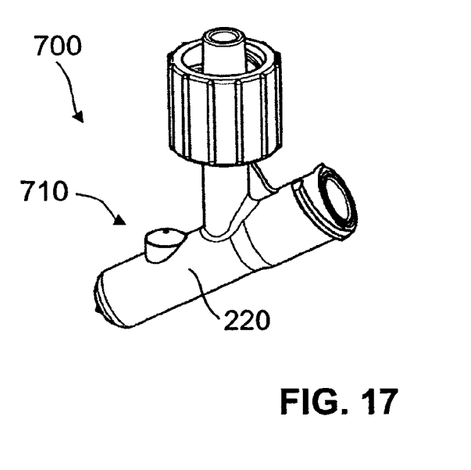
FIG. 17 a perspective view of a spray head according to a fifth exemplary embodiment of the present invention.
Figure 18:
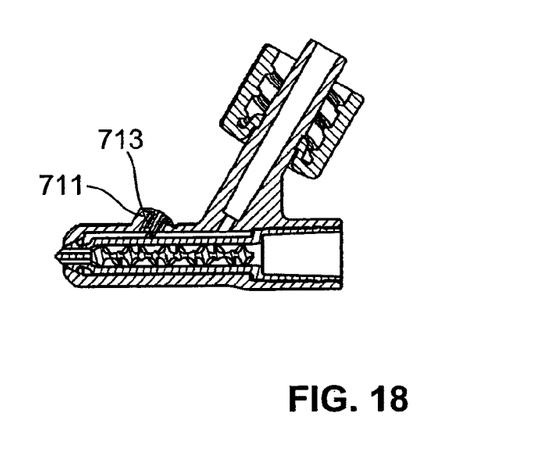
FIG. 18 a central longitudinal section of the spray head of FIG. 17.
Figure 19:
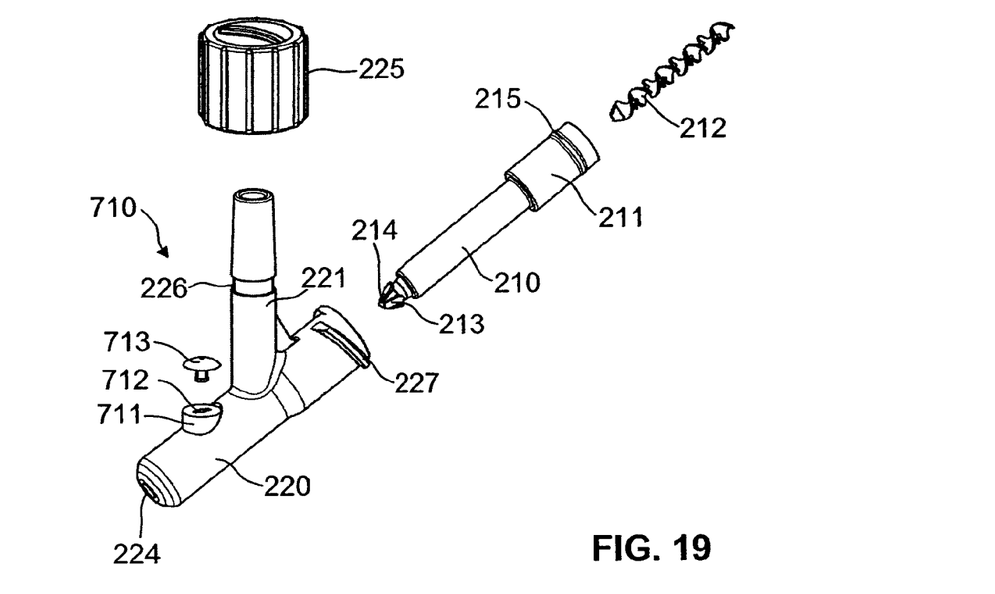
FIG. 19 a perspective disaggregated component drawing of the spray head of FIG. 17.
Figure 20:
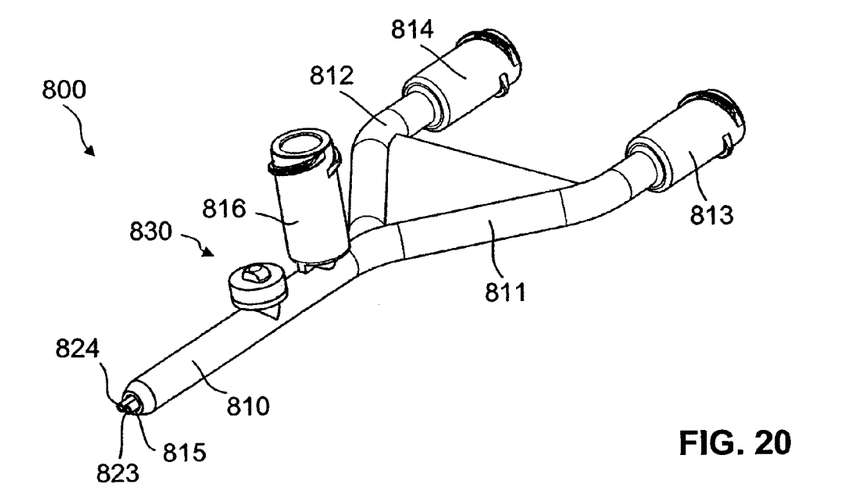
FIG. 20 a perspective view of a spray head according to a sixth exemplary embodiment of the present invention.
Figure 21:
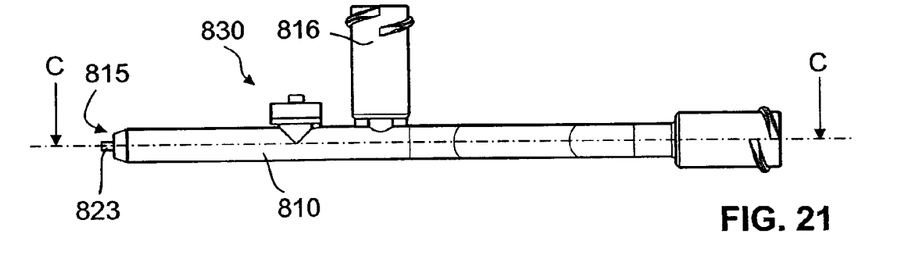
FIG. 21 a lateral view of the spray head of FIG. 20.
Figure 22:
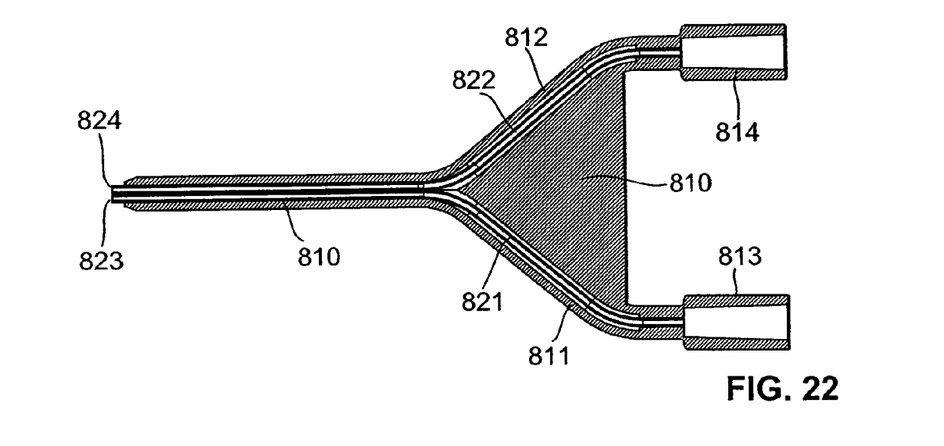
FIG. 22 a central longitudinal section of the spray head in the plane C-C of FIG. 21.
Figure 23:
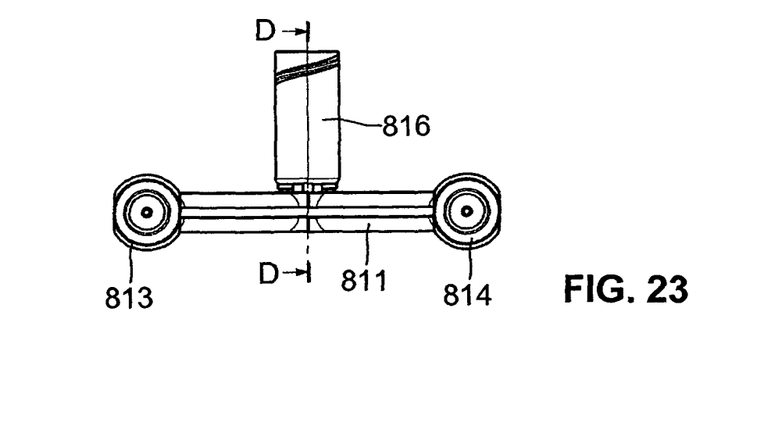
FIG. 23 a view of the spray head of FIG. 20 from the proximal end.
Figure 24:
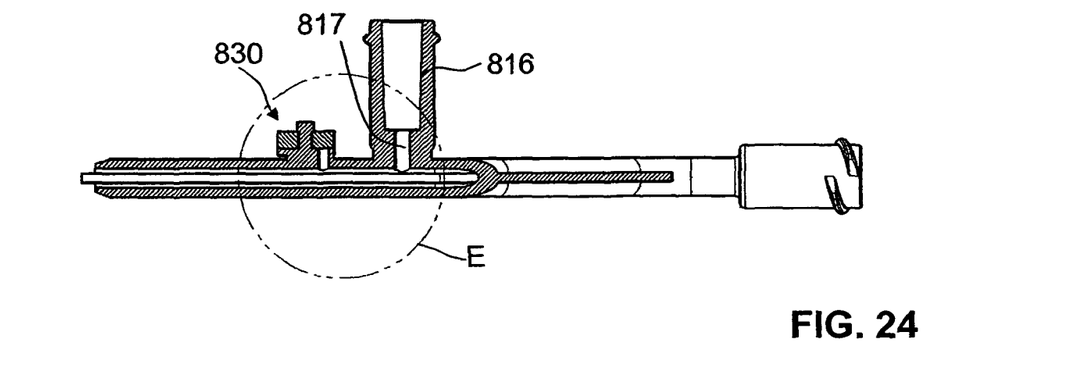
FIG. 24 a central longitudinal section of the spray head in the plane D-D of FIG. 23.
Figure 25:
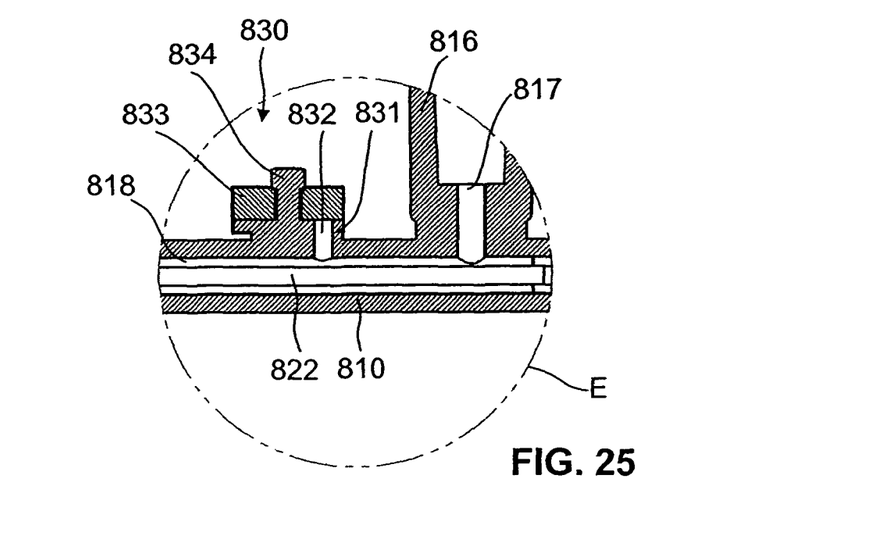
FIG. 25 a detailed view of FIG. 24 in the region E.

FIGS. 17 to 19 illustrate a fifth exemplary embodiment of the present invention. The spray head 700 comprises a pressure relief valve 710 that is designed as an umbrella valve or mushroom-shaped valve. In a valve base 711 a central valve outlet channel 712 is formed that has a shape that is not rotationally symmetrical. A mushroom-shaped valve body 713 comprising an elastic material, e.g. silicon, has been inserted into this channel 712. An umbrella-like upper region of the valve body 713 covers the valve outlet channel, provided a threshold pressure is not exceeded. When the threshold pressure is exceeded, the pressure-related force lifts the umbrella-like region of the valve body 713 from the valve outlet channel so that the compressed gas can escape from the valve outlet channel. In this type of valve the threshold pressure can be set within a wide range by suitable dimensioning of the valve outlet channel and by a suitable selection of the preload/bias, the dimensions and the material of the valve body.

A sixth exemplary embodiment is illustrated in FIGS. 20 to 25. The spray head 800 shown in this embodiment has a fundamentally different design than the spray heads in the previous exemplary embodiments. The present exemplary embodiment illustrates that the invention can be implemented with spray heads of a host of different designs.

The spray head 800 comprises a Y-shaped basic body which towards the distal end of the spray head comprises an elongated cylindrical distal tube 810. Towards the proximal end of the spray head this tube 810 splits into two curved inlet tubes 811, 812 that together form a V-shaped arrangement. At their proximal ends these inlet tubes in each case comprise a fluid connector 813, 814 in the form of a female Luer connector. From each of these fluid connectors a curved interior tube 821, 822, e.g. comprising metal, or a flexible hose in each case extends through an inlet tube 811, 812 and through the distal tube 810 to the distal end of the spray head, where the interior tubes in each case end at a fluid outlet 823, 824; in this manner each of these interior tubes forms a fluid channel that in each case extends from a fluid connector 813, 814 to a fluid outlet 823, 824 at the distal end of the spray head. The external diameters of these two interior tubes 821, 822 are significantly smaller than the internal diameter of the distal tube 810. The space between the interior tubes 821, 822 and the delimitation wall of the distal tube 810 in this manner forms a gas distribution channel 818 (see FIG. 25).

At the tube 810, adjacent to the position at which the two inlet tubes 811, 812 meet, a compressed gas connector 816 in the form of a female Luer connection is arranged, which compressed gas connector 816 leads to a gas supply channel 817. This gas supply channel 817 connects the compressed gas connector to the gas distribution channel 818. At the distal end of the spray head the gas distribution channel ends in a gas outlet opening 815 that is arranged so as to be set back slightly, in the proximal direction, from the fluid outlets 823, 824 that are formed by the ends of the interior tubes 821, 822.

This spray head is suitable, in particular, to spray the components of a medical two-component adhesive by means of a compressed gas. To this effect a fluid reservoir, in each case comprising one of the components to be sprayed, is connected to each of the fluid connectors 813, 814. In particular, for example, the outlets of a double syringe can be connected to the fluid connectors. A hose for supplying a compressed gas is connected to the compressed gas connector 816. The compressed gas flows through the gas supply channel 817 and the gas distribution channel 818 to the gas outlet opening 815, thus generating a gas flow in the region of the fluid outlets 823, 824. At this stage a user dispenses in a suitable manner the components from the two fluid reservoirs so that these components are fed through the interior tubes 821, 822 to the fluid outlets 823, 824, where they exit. In the case of a double syringe such dispensing takes place, for example, by means of manual pressure onto the interconnected piston rods of the double syringe. As soon as the components issue from the fluid outlets 823, 824 they are atomised by the gas flow so that they form small droplets, thus in the form of a fine spray mist reaching an application region.

Near the proximal end of the tube 810 a pressure relief valve 830 is formed that essentially has a design that is identical to that of the pressure relief valve of the first exemplary embodiment (FIGS. 4 to 7). In particular this embodiment, too, comprises a valve base 831 with a valve outlet channel 832 arranged decentrally. An elastic valve disc 833, which is held to the valve base 831 by means of a central holding structure 834, closes the valve outlet channel 832 towards the outside. If a threshold pressure is exceeded, the valve disc is lifted from the valve outlet channel 832 against its elastic restoring force, thus opening said valve outlet channel 832. In this exemplary embodiment, too, in this manner any build-up of damaging overpressure can be effectively prevented.

As is clearly evident from the above exemplary embodiments, the invention is by no means limited to a particular design of a spray head. The invention can be realised on any spray head known per se, which spray head comprises one or several connectors for one or several fluid reservoirs and comprises a compressed gas connector. The invention is largely independent of the specific topology of the spray head. It can even be implemented on spray heads in which the compressed gas is fed through a central compressed gas channel in the spray head, while the components to be sprayed are guided in a region enclosing the compressed gas channel, as is the case, for example, in the spray head of U.S. Pat. No. 5,605,541, or in which spray heads the components to be sprayed are dispensed in a mixing chamber to which the compressed gas is centrally supplied, as is the case, for example, in US 2003/0209612. In this case it may make sense to provide the pressure relief valve in the region of the compressed gas connector before the compressed gas enters the central compressed gas channel.

From the above exemplary embodiments it also becomes evident that the invention is by no means limited to a particular type of pressure relief valve. While the valves that have been explicitly described above due to their simple design and their economic manufacture are preferred, other types of pressure relief valves that open when a defined threshold pressure is exceeded can be used. Such pressure relief valves are known in a host of different designs from the state of the art.

While the spray heads presented above in each case feature a comparatively short design, the invention is by no means limited to such short designs. The invention can, in particular, also be used with spray heads that are intended for endoscopic or minimal-invasive applications, and for this reason in a distal region comprise an elongated tubular design. In terms of such designs, reference is made, for example, to U.S. Pat. No. 5,810,885, US 2009/0209916 or US 2009/0199848. In such spray heads it is preferred if the pressure relief valve is provided in a proximal region upstream of the elongated-tubular distal region.

The invention claimed is:

1. A spray head for spraying at least one fluid substance with the use of compressed gas, comprising:
   at least one fluid connector in order to connect the spray head to at least one fluid reservoir for the substance to be sprayed;
   at least one fluid channel that connects the fluid connector to at least one fluid outlet;
   a compressed gas connector in order to connect the spray head to a source of compressed gas;
   at least one compressed gas channel that connects the compressed gas connector to at least one compressed gas outlet; and
   a pressure relief valve that is configured to discharge compressed gas directly from the compressed gas channel when the compressed gas has a gas pressure that exceeds a threshold pressure, the pressure relief valve being directly arranged on the spray head itself, wherein the fluid outlet and the compressed gas outlet are arranged relative to each other in such a manner that during operation compressed gas exiting the compressed gas outlet mixes with a substance exiting the fluid outlet in order to spray the substance.

2. The spray head according to claim 1, wherein the pressure relief valve is arranged on the spray head itself in a region of the compressed gas channel, which region in terms of the direction of flow of the compressed gas is arranged upstream of the compressed gas outlet.

3. The spray head according to claim 1, wherein the pressure relief valve is arranged on the spray head itself in a region of the compressed gas channel, which region in terms of the direction of flow of the compressed gas is arranged downstream of the compressed gas connector.

4. The spray head according to claim 1, wherein the pressure relief valve is arranged on the spray head itself in a region of the compressed gas channel, which region at least partly encloses the fluid channel.

5. The spray head according to claim 1, wherein the spray head comprises a static mixing element that is arranged in the fluid channel.

6. The spray head according to claim 5, wherein the pressure relief valve is provided on the spray head itself in a region of the compressed gas channel, which region at least partly encloses the region of the fluid channel, in which region the static mixing element is arranged.

7. The spray head according to claim 1, wherein the spray head comprises a basic body and a gas feed pipe that protrudes from the basic body, on which gas feed pipe the compressed gas connector is provided, and wherein the pressure relief valve is provided on the basic body and comprises a valve outlet channel that extends so as to be essentially parallel to the gas feed pipe.

8. The spray head according to claim 7, wherein the gas feed pipe is integrally formed with the basic body.

9. The spray head according claim 1, wherein the spray head comprises an inner sleeve in which the at least one fluid channel is formed, and an outer sleeve that at least partly encloses the inner sleeve, wherein the outer sleeve and the inner sleeve together delimit at least one section of the compressed gas channel, and wherein both the compressed gas connector and the pressure relief valve are formed on the outer sleeve.

10. The spray head according to claim 9, wherein the outer sleeve defines a longitudinal axis, and wherein the pressure relief valve comprises a valve outlet channel whose longitudinal direction is arranged relative to the longitudinal axis of the outer sleeve 220 at an angle of between 30° and 90°.

11. The spray head according to claim 1, wherein the spray head comprises a basic body and a gas feed pipe that protrudes from the basic body, which gas feed pipe comprises the compressed gas connector, and wherein the pressure relief valve is arranged on the gas feed pipe.

12. The spray head according to claim 1, wherein the spray head is designed to spray a medical product or components of a medical product.

13. The spray head according to claim 1, wherein the pressure relief valve comprises an elastic closure body that is attached to a valve base in such a manner that because of its intrinsic elasticity it closes a valve outlet channel, provided the gas pressure does not exceed the threshold pressure.

14. The spray head according to claim 1, wherein the pressure relief valve comprises a rigid, movable closure body that is spring-loaded in such a manner that it closes a valve outlet channel, provided the gas pressure does not exceed the threshold pressure.

15. The spray head according to claim 1, wherein the pressure relief valve comprises an elastic sleeve that encloses a tubular section of the spray head on the outside, and due to its elasticity closes at least one valve outlet channel formed in the tubular section, provided the gas pressure does not exceed the threshold pressure.

16. The use of a spray head according to claim 1 for spraying a medical product or components of a medical product.

17. The spray head according to claim 1, wherein the pressure relief valve is integrally formed with the spray head.

18. The spray head according to claim 17, wherein a compressed gas hose is connected to the compressed gas connector in order to supply the compressed gas from the source of compressed gas to the spray head.

19. A spray head for spraying at least one fluid substance with the use of compressed gas, comprising:
   a first fluid connector and a second fluid connector, wherein each of the fluid connectors is designed to connect the spray head with a respective fluid reservoir for a component to be sprayed;
   a first fluid channel that connects the first fluid connector to a first fluid outlet;
   a second fluid channel that connects the second fluid connector to a second fluid outlet;
   a compressed gas connector in order to connect the spray head to a source of compressed gas;
   at least one compressed gas channel that connects the compressed gas connector to at least one compressed gas outlet; and
   a pressure relief valve that is configured to discharge compressed gas directly from the compressed gas channel when the compressed gas has a gas pressure that exceeds a threshold pressure, the pressure relief valve being directly arranged on the spray head itself,
   wherein the first fluid outlet, the second fluid outlet and the compressed gas outlet are arranged relative to each other in such a manner that during operation compressed gas exiting the compressed gas outlet mixes with the two components exiting the fluid outlets in order to spray both the components.

20. The spray head according to claim 19, wherein the pressure relief valve is integrally formed with the spray head.

21. A spray device for spraying a medical adhesive, comprising:
   A. a spray head for spraying at least one fluid substance with the use of compressed gas, the spray head comprising:
      at least one fluid connector in order to connect the spray head to at least one fluid reservoir for the substance to be sprayed;
      at least one fluid channel that connects the fluid connector to at least one fluid outlet;
      a compressed gas connector in order to connect the spray head to a source of compressed gas;
      at least one compressed gas channel that connects the compressed gas connector to at least one compressed gas outlet; and
      a pressure relief valve that is configured to discharge compressed gas directly from the compressed gas channel when the compressed gas has a gas pressure that exceeds a threshold pressure, the pressure relief valve being directly arranged on the spray head itself,
      wherein the fluid outlet and the compressed gas outlet are arranged relative to each other in such a manner that during operation compressed gas exiting the compressed gas outlet mixes with a substance exiting the fluid outlet in order to spray the substance, B. at least one fluid reservoir with a medical adhesive contained therein, wherein the spray head is connectable to the fluid reservoir; and C. a dispensing device for dispensing the adhesive through the spray head.

22. The spray device according to claim 21, wherein the pressure relief valve is integrally formed with the spray head.

23. A spray device for spraying at least two components of a medical adhesive, comprising:

A. a spray head for spraying at least one fluid substance with the use of compressed gas, the spray head comprising:

a first fluid connector and a second fluid connector, wherein each of the fluid connectors is designed to connect the spray head with a respective fluid reservoir for a component to be sprayed;

a first fluid channel that connects the first fluid connector to a first fluid outlet;

a second fluid channel that connects the second fluid connector to a second fluid outlet;

a compressed gas connector in order to connect the spray head to a source of compressed gas;

at least one compressed gas channel that connects the compressed gas connector to at least one compressed gas outlet; and a pressure relief valve that is configured to discharge compressed gas directly from the compressed gas channel when the compressed gas has a gas pressure that exceeds a threshold pressure, the pressure relief valve being directly arranged on the spray head itself, wherein the first fluid outlet, the second fluid outlet and the compressed gas outlet are arranged relative to each other in such a manner that during operation compressed gas exiting the compressed gas outlet mixes with the two components exiting the fluid outlets in order to spray both the components;

B. at least two fluid reservoirs, each fluid reservoir comprising a component of the medical adhesive contained therein, wherein the spray head is adapted to be connected to the fluid reservoirs; and C. a dispensing device for dispensing the components through the spray head.

24. A method for spraying a medical product, comprising: providing the medical product in a reservoir;

providing a spray head with at least one fluid connector, a compressed gas connector and a pressure relief valve, the pressure relief valve being directly arranged on the spray head itself;

connecting the fluid connector of the spray head to an outlet of the reservoir;

supplying compressed gas to the compressed gas connector of the spray head so that the compressed gas flows out through at least one compressed gas outlet of the spray head;

dispensing the medical product through at least one fluid outlet of the spray head in order to spray the product by means of the compressed gas; and releasing compressed gas directly from a compressed gas channel of the spray head through the pressure relief valve if the pressure relief valve opens.

25. The method according to claim 24, wherein the spraying process is terminated if the pressure relief valve opens.

26. The method according to claim 24, wherein the medical product is a medical adhesive.

27. A method for spraying at least two components of a medical product, comprising:

providing the components of the medical product in each case in a reservoir comprising in each case at least one outlet;

providing a spray head with at least two fluid connectors, a compressed gas connector and a pressure relief valve the pressure relief valve being directly arranged on the spray head itself;

connecting the fluid connectors of the spray head to the outlets of the reservoir;

supplying compressed gas to the compressed gas connector of the spray head so that the compressed gas flows out through at least one compressed gas outlet of the spray head;

dispensing the components through fluid outlets of the spray head in order to spray the components by means of the compressed gas; and releasing compressed gas directly from a compressed gas channel of the spray head through the pressure relief valve if the pressure relief valve opens.

28. The method according to claim 27, wherein the spraying process is terminated if the pressure relief valve opens.

29. The method according to claim 27, wherein the medical product is a medical adhesive.

* * * * *